(12) United States Patent
Broqua

(10) Patent No.: US 7,115,650 B1
(45) Date of Patent: Oct. 3, 2006

(54) COMPOSITIONS FOR IMPROVING FERTILITY

(75) Inventor: Pierre Broqua, Thoiry (FR)

(73) Assignee: Ferring BV, Hoofddorp (NL)

( * ) Notice: Subject to any disclaimer, the term of this patent is extended or adjusted under 35 U.S.C. 154(b) by 0 days.

(21) Appl. No.: 09/937,032

(22) PCT Filed: Mar. 21, 2000

(86) PCT No.: PCT/IB00/00382

§ 371 (c)(1), (2), (4) Date: Jan. 3, 2002

(87) PCT Pub. No.: WO00/56296

PCT Pub. Date: Sep. 28, 2000

(30) Foreign Application Priority Data

Mar. 23, 1999 (GB) .................... 9906714.2

(51) Int. Cl.
*A61K 31/40* (2006.01)

(52) U.S. Cl. .................................... 514/423

(58) Field of Classification Search ............... 514/423
See application file for complete search history.

(56) References Cited

FOREIGN PATENT DOCUMENTS

| WO | 91/16339 | 10/1991 |
|---|---|---|
| WO | 93/08259 | 4/1993 |
| WO | 95/15309 | 6/1995 |
| WO | 98/19998 | 5/1998 |
| WO | 98/25644 | 6/1998 |

OTHER PUBLICATIONS

Ashworth, D.M. et al. "2-Cyanopyrrolidides As Potent, Stable Inhibitors of Dipeptidyl Peptidase IV," *Biororg. Med. Chem. Lett.* (1996), vol. 6, No. 10, pp. 1163-1166.

Bongers, J. "Kinetics of dipeptidyl peptidase IV proteolysis of growth hormone-releasing factor and analogs," *Biochem. Biophys. Acta.* (1992), vol. 1122, No. 2, pp. 147-153.

Mentlein, R. "Dipeptidyl-peptidase IV (CD26)-role in the inactivation of regulatory peptides," *Regulatory Peptides* (1999), vol. 85, No. 1, pp. 9-24.

Artini, P.G. et al. "Clinical Utility of Adjuvant Growth Hormone in the Treatment of Patients with Polycystic Ovaries Undergoing in Vitro Fertilization," *Journal of Assisted Reproduction and Genetics* (1997), vol. 14, No. 1, pp. 4-7.

Lee, K.O. "Growth Hormone Treatment in Infertility: A Short Review," *Indian Journal of Pediatrics* (1991), vol. 58, Suppl. No. 1, pp. 51-56.

Landolfi, L. et al. "Induzione Dell'Ovulazione Con Ormone Della Crescita E GnRH Nell' Ovaio Policistico," *Rassegna Internazionale Di Clinica E Terapia* (1994), vol. 74, No. 12, pp. 529-532.

*Primary Examiner*—San-Ming Hui
(74) *Attorney, Agent, or Firm*—Foley & Lardner LLP

(57) ABSTRACT

Inhibitors of dipeptidyl peptidase IV and pharmaceutical compositions comprising these inhibitors are useful in the treatment of infertility, and particularly human female infertility due to polycystic ovary syndrome.

8 Claims, No Drawings

COMPOSITIONS FOR IMPROVING FERTILITY

The present invention relates to agents and compositions for improving animal fertility, especially in females, usually human.

Inhibitors of DP-IV

Dipeptidyl peptidase IV (DP-IV, also dipeptidyl aminopeptidase IV, DPP-IV, DAP-IV, EC 3.4.14.5) is a serine peptidase that cleaves the amino-terminal dipeptide from peptides and proteins. It recognises substrates wherein the N-terminal sequence is X-Pro or X-Ala. Inhibitors of DP-IV have been proposed as therapeutic agents for the treatment of inflammatory diseases and AIDS. Generally, the known inhibitors of DP-IV are analogues of the substrate. Examples of DP-IV inhibitors are those disclosed in DD 296 075 A5 (Neubert et al., November 1991), WO91/16339 (Bachovchin et al., October 1991), WO93/08259 (Bachovchin et al., April 1993), WO95/15309 (Jenkins et al., June 1995), WO98/19998 (Villhauer, May 1998), WO99/46272 (Scharpe et al., September 1999) and WO99/61431 (Demuth et al., December 1999). Prodrugs of some of these inhibitors have also been described in WO99/67278 and WO99/67279 (both Demuth et al., December 1999).

The following table sets out general types of DP-IV inhibitor compounds, and specific examples thereof which are amongst those preferred for use in the present invention; it also indicates the patent publications from whose broader range of disclosed compounds these types and examples are drawn. It is emphasised that all DP-IV inhibitors disclosed in the quoted DD and WO specifications can be used in the present invention, and reference is positively directed to these prior specifications for full information on the general and more specific formulae and individual compounds concerned. For example, in the table below the indicated pyrrolidine and thiazolidine rings can be replaced by a wide range of other heterocycles of various ring sizes and/or the indicated amino-acyl moieties can be replaced by a wide range of others, as taught by the indicated publications, to give other DP-IV inhibitors for use in the present invention.

Amino-acyl pyrrolidides and thiazolidides (see DD 296 075 A5), e.g.

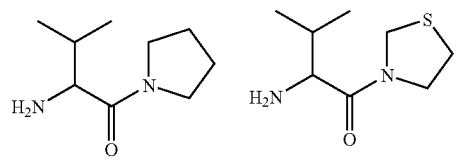

Amino-acyl pyrrolidine aldehydes (see DD 296 075 A5 and WO95/15309), e.g.

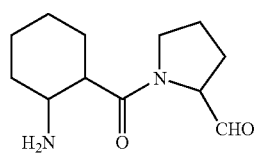

Amino-acyl pyrrolidine boronic acids (see WO91/16339 and WO93/08259), e.g.

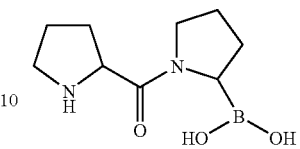

Amino-acyl pyrrolidine nitriles (see WO95/15309 and WO98/19998), e.g.

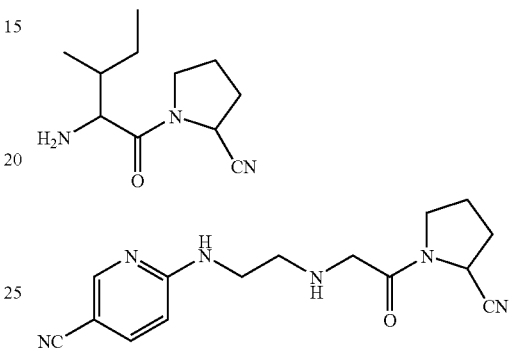

Polycystic Ovary Syndrome

Polycystic ovary syndrome (PCOS, Stein-Leventhal syndrome) is a condition characterized by thickening of the ovarian capsule and formation of multiple follicular cysts. It results in infertility and amenorrhea. The levels of circulating hormones are disturbed—luteinizing hormone (LH) and steroids are elevated and follicle stimulating hormone (FSH) is decreased. Although it has been suggested that this is a consequence of abnormal secretion of gonadotropin releasing hormone (GnRH) from the hypothalamus, the physiological defect underlying PCOS remains the subject of speculation. The use of treatment regimens that control the levels of LH and FSH can lead to successful assisted fertilization, but such regimens tend to be complex and expensive. We have now found that DP-IV inhibitors demonstrate utility in the treatment of PCOS.

A first aspect of the present invention is a pharmaceutical composition for the treatment of infertility, which composition is characterized by the inclusion of inhibitor of DP-IV. A second aspect of the present invention is a novel use of inhibitors of DP-IV, namely in the treatment of infertility, and particularly human female infertility due to PCOS. A third aspect of the invention is an improved protocol for assisted fertilization in subjects with PCOS, wherein the subject is administered a composition comprising DP-IV inhibitor.

The use of DP-IV inhibitors in this way presents many advantages over current treatment regimens that include GnRH agonists as well as FSH and LH. LH and FSH are large peptides that are either isolated from natural sources (generally the urine of post-menopausal women) or prepared in culture using recombinant cells. Isolation from urine requires that attention be paid to risk of disease transmission and the presence of antigenic protein contaminants. Recombinant hormones are less likely to transmit human pathogens but are still potentially contaminated with antigenic protein, and are considerably more expensive than urinary proteins. Furthermore, recombinant peptides do not generally have a completely "humanized" glycosylation pattern, which might lead to antigenicity and reduced efficacy. GnRH agonists are generally decapeptides, which require multistep synthesis. In contrast, DP-IV inhibitors are small molecules that are readily accessible using standard synthetic methods. They are non-antigenic, easy to purify and inexpensive. A further advantage is that DP-IV inhibitors are in many cases biologically active after oral administration. This is in contrast to GnRH agonists, FSH and LH, which must all be administered by injection. Hence the use of DP-IV inhibitors leads to a less invasive protocol that is less stressful for the patient.

The pharmaceutical composition of the present invention is particularly effective for the treatment of infertility in human females. Preferably the infertility is associated with polycystic ovary syndrome. The composition is characterized in that it comprises inhibitor of DP-IV. The composition may further include such pharmaceutically acceptable excipients as are generally known in the art, such as diluents, carriers, bulking agents, binding agents, dispersants, stabilizers and the like.

In the context of the present invention, a compound is considered to be an inhibitor of DP-IV if it inhibits the action of the enzyme at a concentration of 1 µM. Preferably, such a compound inhibits the action of DP-IV at concentrations below 100 nM and does not inhibit other enzymes at concentrations below 1 µM. The following table sets out general types of DP-IV inhibitor compounds, and specific examples thereof which are amongst those preferred for use in the present invention; it also indicates the patent publications from whose broader range of disclosed compounds these types and examples are drawn. It is emphasised that all DP-IV inhibitors disclosed in the quoted DD and WO specifications can be used in the present invention, and reference is positively directed to these prior specifications for full information on the general and more specific formulae and individual compounds concerned. For example, in the table below the indicated pyrrolidine and thiazolidine rings can be replaced by a wide range of other heterocycles of various ring sizes and/or the indicated amino-acyl moieties can be replaced by a wide range of others, as taught by the indicated publications, to give other DP-IV inhibitors for use in the present invention.

Amino-acyl pyrrolidides and thiazolidides (see DD 296 075 A5), e.g.

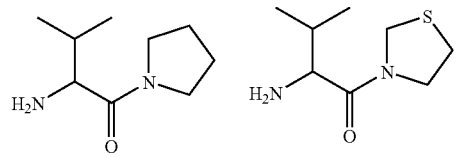

Amino-acyl pyrrolidine aldehydes (see DD 296 075 A5 and WO95/15309), e.g.

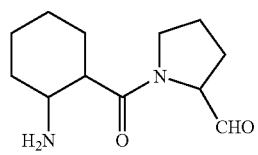

Amino-acyl pyrrolidine boronic acids (see WO91/16339 and WO93/08259), e.g.

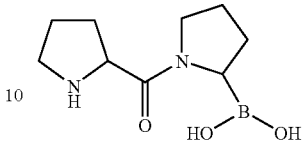

Amino-acyl pyrrolidine nitriles (see WO95/15309 and WO98/19998), e.g.

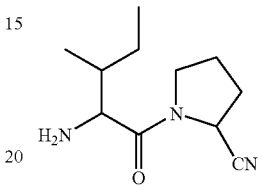

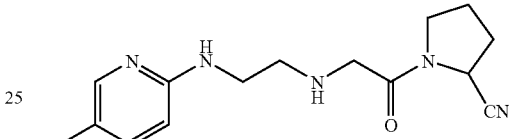

In a preferred embodiment of the invention, the inhibitor of DP-IV is an amino-acylpyrrolidine nitrile. Particularly preferred are those amino-acyl pyrrolidine nitrites disclosed in WO95/15309 and WO98/19998.

The compositions according to the present invention may be formulated for administration to human subjects by any of the known routes, including oral administration, transmucosal administration (such as buccal, sublingual, intranasal, vaginal and rectal administration), transdermal administration or injection (including intravenous, intramuscular and subcutaneous injection). A preferred route of administration is oral administration. In this case the composition is suitably formulated as a tablet or capsule.

The present invention provides a new use for compounds that are known to be inhibitors of DP-IV, which is as therapeutic agents for the treatment of infertility, and particularly human female infertility due to polycystic ovary syndrome.

The present invention comprises an improved method for the treatment of infertility, particularly human female infertility due to PCOS, wherein the patient is administered a pharmaceutical composition comprising a therapeutically effective amount of inhibitor of DP-IV. The treatment may involve the use of said composition alone or in conjunction with other agents such as have been described heretofore. The administration may be as a single dose or as divided doses taken at intervals of, for example, 2–6 hours. The course of treatment might last a single day or for a period of several days or weeks until a suitable clinical endpoint has been reached. Examples of suitable endpoints include conception (in the case of unassisted fertilisation) and successful harvest of unfertilised ova or successful implantation of the embryo (in the case of assisted fertilisation). The details of the dosing regimen and treatment duration will be determined by the responsible physician.

EXAMPLES

Example 1

Preparation of Inhibitors

The inhibitors of DP-IV can be prepared following the methods outlined in the literature. The synthesis of aminoacyl pyrrolidine nitrites is described in WO95/15309 and WO98/19998. The following method is illustrative of these methods.

Example 1A

Synthesis of (2S)-N-isoleucylpyrrolidine-2-carbonitrile

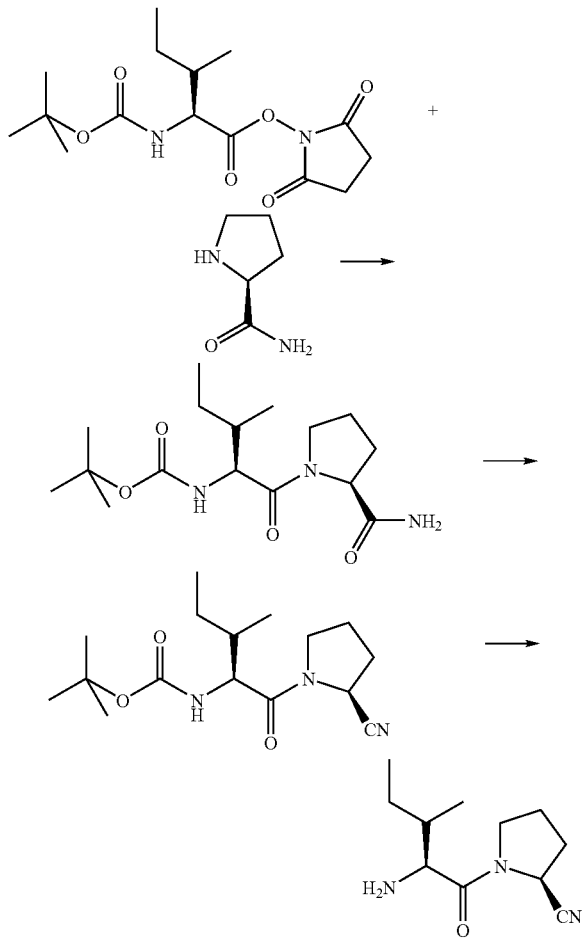

(a) tert-Butyloxycarbonyl-isoleucylprolinamide

To a stirred suspension of prolinamide hydrochloride (225 mg, 1.50 mmol) in dry dichloromethane (15 mL) was added diisopropylethylamine to give a clear basic (pH 9) solution. N-(tert-Butyloxycarbonyl-isoleucyloxy)succinimide (328 mg, 1.0 mmol) was added in one portion and the mixture was stirred at room temperature for 16 hours under a nitrogen atmosphere. The solvent was evaporated in vacuo and the residue was partitioned between ethyl acetate and 0.3N potassium hydrogensulphate solution. The organic layer was washed with saturated sodium hydrogencarbonate solution, water and brine, dried over sodium sulphate, and concentrated in vacuo. The residue was purified by filtration through a short plug of silica gel, eluting with hexane/ethyl acetate (10:90) then ethyl acetate. Concentration of the product-containing eluate gave the title compound as a colourless foaming glass; 301 mg (92%).

$^1$H NMR (CDCl$_3$): δ 6.90 (1H, br. s); 5.51 (1H, br. s); 5.18 (1H, d, J=9.6 Hz); 4.62 (1H, dd, J=2.6 & 7.0 Hz); 4.29 (1H, dd, J=8.4 & 9.2 Hz); 3.79–3.58 (2H, m); 2.36 (1H, m); 2.09–1.57 (5H, m); 1.43 (9H, s); 1.17 (1H, m); 0.95 (3H, d, J=6.6 Hz); 0.90 (3H, t, J=7.3 Hz) ppm.

(b) (2S)-N-(tert-Butyloxycarbonyl-isoleucyl)pyrrolidine-2-carbonitrile

To a stirred solution of the amide of part (a) (203 mg, 0.62 mmol) in dry pyridine (10 mL) under a nitrogen atmosphere was added imidazole (84 mg, 1.24 mmol). The mixture was cooled to −35° C. and then phosphorus oxychloride (0.25 mL, 2.48 mmol) was added dropwise. The mixture was stirred for 1 hour, during which time the temperature was allowed to rise to −20° C., and the solvent was evaporated in vacuo. The residue was purified by chromatography on silica gel to give the title compound as a colourless oil; yield 180 mg (94%).

$^1$H NMR (CDCl$_3$): δ 5.14 (1H, d, J=9.2 Hz); 4.80 (1H, dd, J=2.6 & 7.1 Hz); 4.22 (1H, dd, J=7.9 & 9.1 Hz); 3.81 (1H, m); 3.71 (1H, m); 2.30–2.12 (4H, m); 1.75 (1H, m); 1.60 (1H, m); 1.42 (9H, s); 1.19 (1H, m); 0.97 (3H, d, J=6.9 Hz); 0.91 (3H, t, J=7.3 Hz) ppm.

$^{13}$C NMR (CDCl$_3$): δ 171.7; 155.6; 118.0; 79.6; 56.0; 46.5; 46.0; 37.8; 29.6; 28.1; 25.0; 24.2; 15.2; 10.9 ppm.

(c) (2S)-N-(Isoleucyl)-pyrrolidine-2-carbonitrile trifluoroacetate

The nitrile of part (b) was dissolved in trifluoroacetic acid and the solution was stirred at room temperature for 1 hour. The solvent was evaporated in vacuo and the residue was dissolved in water. The solution was lyophilised to give the title compound as a white fluffy solid; yield 60 mg.

FAB Mass Spec.: Calculated m/e 209.3; Found 210.2 (M+H)$^+$ $^1$H NMR (D$_2$): δ 4.3 (1H, m); 3.64 (1H, d, J=5.6 Hz); 3.16 (2H, m); 1.86–1.48 (5H, m); 0.98 (1H, m); 0.68 (1H, m); 0.51 (3H, d, J=6.9 Hz); 0.38 (3H, t, J=7.3 Hz) ppm.

$^{13}$C NMR (D$_2$O): δ 169.7; 119.7; 57.3; 48.6; 48.1; 36.9; 30.2; 25.8; 24.5; 15.4; 11.5 ppm.

Example 1B

Synthesis of (2S)-N-((2'S)-2'-amino-3',3'-dimethylbutanoyl)pyrrolidine-2-carbonitrile

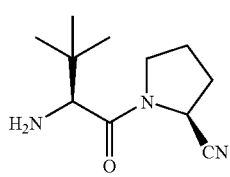

This was prepared following the method of Example 1A by replacing the isoleucine derivative with the corresponding tert-butylglycine derivative.

$^1$H NMR (CD$_3$OD): δ 4.86–4.81(1H, m); 4.04(1H, s); 3.77–3.71(2H, m); 3.34(2H, s); 2.34–2.08(4H, m); 1.14(9H, s) ppm.

$^{13}$C NMR (CD$_3$OD): δ 167.40, 117.99, 58.78, 46.53, 34.21, 29.54, 25.22, 25.03 ppm.

Example 2

Animal Model of Human Infertility

Zucker Diabetic Fatty (ZDF) rats are considered to be an appropriate model for demonstrating the potential utility of therapeutic agents in human fertility, particularly that due to PCOS. The hormonal status of these animals changes as they become obese, which is a parallel with the human disease, where obesity has been suggested as being linked to PCOS.

Animals

Obese Zucker Diabetic Fatty males and females as well as fertile lean males and females were put into individual cages and fed with Purina 5008 (6.5% fat). At 6.5 weeks of life, obese rats were randomized into 3 groups:

1. Control group—obese ZDF rats (n=8) treated with vehicle.
2. Once-daily treatment group—obese ZDF rats (n=8) given the compound of Example 1B orally once daily (10 mg/kg/day).
3. Twice-daily treatment group—obese ZDF rats (n=8) given the compound of Example 1B orally twice daily (10 mg/kg/day).

Methods

Blood and pituitaries of lean and obese rats were collected at the end of the study. Pituitary LH and plasma testosterone concentrations were measured by radioimmunoassay. Estrous cyclicity was evaluated by observation of vaginal smear.

2.1—Pituitary LH

Pituitaries of obese rats contained more LH than lean rats (8.1±0.6 μg/pituitary vs 6.3±0.6 μg/pituitary, for the obese and lean rats, respectively; $p<0.05$). Treatment of obese rats with the compound of Example 1B normalised pituitary LH content to lean values (8.1±0.6 μg/pituitary vs 5.2±0.4 μg/pituitary, for the control and treated obese rats respectively, $p<0.05$).

2.2—Plasma Testosterone

Plasma testosterone levels in obese males were lower than in lean males (1145±328 ng/mL vs 2410±239 ng/mL, for the obese and lean rats respectively; $p<0.05$). Treatment of obese rats with the compound of Example 1B normalised plasma testosterone levels to lean values (2410±239 ng/mL vs 2392±759 ng/mL, for the lean and treated obese rats respectively, NS).

2.3—Cyclicity

Obese females had abnormal estrous cyclicity in comparison to lean rats. Treatment with the compound of Example 1B normalised estrous cyclicity in obese female rats.

The results obtained indicate that inhibitors of DP-IV are useful in the treatment of infertility in both female and male subjects, and particularly in PCOS.

Example 3

Pharmaceutical Formulation

3A—50 mg Tablet

Tablets containing the equivalent of 50 mg of the compound of Example 1A as the active agent are prepared from the following:

| | |
|---|---|
| Compound of Example 1A (as trifluoroacetate salt) | 154.5 g |
| Corn starch | 53.5 g |
| Hydroxypropylcellulose | 13.5 g |
| Carboxymethylcellulose calcium | 11.0 g |
| Magnesium stearate | 2.0 g |
| Lactose | 165.5 g |
| Total | 400.0 g |

The materials are blended and then pressed to give 2000 tablets of 200 mg, each containing the equivalent of 50 mg of the free base of the compound of Example 1A.

3B—100 mg Vaginal Suppository

Suppositories suitable for vaginal administration and containing the equivalent of 100 mg of the compound of Example 1A as the active agent are prepared from the following:

| | |
|---|---|
| Compound of Example 1A (as trifluoroacetate salt) | 154.5 g |
| Corn starch | 210.0 g |
| Colloidal silica | 2.5 g |
| Povidone 30 | 49.0 g |
| Magnesium stearate | 23.0 g |
| Adipic acid | 57.0 g |
| Sodium bicarbonate | 43.0 g |
| Sodium lauryl sulphate | 5.0 g |
| Lactose | 456.0 g |
| Total | 1000.0 g |

The materials are blended and then pressed to give 1000 suppositories of 1 g, each containing the equivalent of 100 mg of the free base of the compound of Example 1A.

The foregoing Examples are illustrative of the invention as disclosed herein, but are not intended to be limiting. Such extensions as would be considered equivalent by one skilled in the art are included within the scope of the invention and the Claims that further define that scope.

One or more DP-IV inhibitors may be used as the sole component active for the specified purposes of the composition and method of the invention.

The invention claimed is:

1. A method of improving fertility, comprising administering to a patient in need thereof a pharmaceutical composition comprising an inhibitor of dipeptidyl peptidase IV, wherein said inhibitor is an amino-acyl pyrrolidine or an amino-acyl thiazolidine.

2. The method according to claim 1, wherein said inhibitor is an amino-acyl pyrrolidine nitrile.

3. The method according to claim 1, wherein said inhibitor is an (2S)-N-isoleucylpyrrolidine-2-carbonitrile or a pharmaceutically active salt thereof.

4. The method according to claim 1, wherein said inhibitor is an (2S)-N-((2'S)-2'-amino-3',3'-dimethylbutanoyl)pyrrolidine-2-carbonitrile or a pharmaceutically active salt thereof.

5. The method according to claim 1, wherein said inhibitor is an amino-acyl pyrrolidine aldehyde.

6. The method according to claim 1, wherein said inhibitor is an amino-acyl pyrrolidine boronic acid.

7. The method according to claim 1, wherein the pharmaceutical composition is formulated for oral administration.

8. The method according to claim 1, wherein the pharmaceutical composition is formulated as a tablet or capsule.

* * * * *